(12) United States Patent
Kakuta

(10) Patent No.: US 10,285,985 B2
(45) Date of Patent: May 14, 2019

(54) PHARMACEUTICAL COMPOSITION FOR TREATMENT OR PREVENTION OF NEURODEGENERATIVE DISEASES

(71) Applicant: NATIONAL UNIVERSITY CORPORATION OKAYAMA UNIVERSITY, Okayama-shi, Okayama (JP)

(72) Inventor: Hiroki Kakuta, Okayama (JP)

(73) Assignee: NATIONAL UNIVERSITY CORPORATION OKAYAMA UNIVERSITY, Okayama-Shi, Okayama (JP)

( * ) Notice: Subject to any disclaimer, the term of this patent is extended or adjusted under 35 U.S.C. 154(b) by 0 days.

(21) Appl. No.: 15/562,509

(22) PCT Filed: Mar. 31, 2016

(86) PCT No.: PCT/JP2016/060714
§ 371 (c)(1),
(2) Date: Sep. 28, 2017

(87) PCT Pub. No.: WO2016/159256
PCT Pub. Date: Oct. 6, 2016

(65) Prior Publication Data
US 2018/0092888 A1 Apr. 5, 2018

(30) Foreign Application Priority Data

Mar. 31, 2015 (JP) .................. 2015-072506

(51) Int. Cl.
*A61K 31/4192* (2006.01)
*A61K 31/4184* (2006.01)
*A61K 31/44* (2006.01)

(52) U.S. Cl.
CPC .......... *A61K 31/44* (2013.01); *A61K 31/4184* (2013.01); *A61K 31/4192* (2013.01)

(58) Field of Classification Search
CPC ................. A61K 31/4192; A61K 31/4184
See application file for complete search history.

(56) References Cited

U.S. PATENT DOCUMENTS

| | | |
|---|---|---|
| 2010/0120742 A1 | 5/2010 | Kakuta et al. |
| 2013/0190395 A1 | 7/2013 | Chandraratna et al. |
| 2014/0329903 A1 | 11/2014 | Burstein et al. |

FOREIGN PATENT DOCUMENTS

| | | |
|---|---|---|
| JP | 2010-111588 A | 5/2010 |
| JP | 2013-177329 A | 9/2013 |
| JP | 2014-076953 A | 5/2014 |
| WO | WO 2008/105386 A1 | 9/2008 |

(Continued)

OTHER PUBLICATIONS

Hiroki Kakuta, et al., "RXR Partial Agonist CBt-PMN Exerts Therapeutic Effects on Type 2 Diabetes without the Side Effects of RXR Full Agonists", American Chemical Society (ACS) Medicinal Chemistry Letters, 2012, pp. 427-432, vol. 3.

Kohei Kawata, et al., "RXR Partial Agonist Produced by Side Chain Repositioning of Alkoxy RXR Full Agonist Retains Antitype 2 Diabetes Activity without the Adverse Effects", Journal of Medicinal Chemistry, 2014, pp. 912-926, vol. 58.

(Continued)

*Primary Examiner* — Samira J Jean-Louis
(74) *Attorney, Agent, or Firm* — Buchanan, Ingersoll & Rooney PC

(57) ABSTRACT

There is provided a pharmaceutical composition for treatment or prevention of a neurodegenerative disease, comprising an RXR agonist as an active ingredient, which is a compound represented by formula (1) or (2). The pharmaceutical composition is effective in treatment or prevention of neurodegenerative diseases such as dementia, Parkinson's disease and multiple sclerosis with reducing side effects such as enlargement of the liver and elevation of blood triglyceride level. In these formulas, A represents $CMe_2$, N-methyl, N-ethyl or N-isopropyl; X represents N, CH or $C-CF_3$; Y and Z represent N or CH; $R^1$ represents methyl, hydroxy, methoxy or ethoxy; $R^2$ represents H, methyl or ethyl; B represents $NR^3$ or $CHR^3$; $R^3$ represents alkyl; and $R^4$ represents H, halogen, alkyl, alkenyl, aryl, alkynyl, alkoxy or acyl.

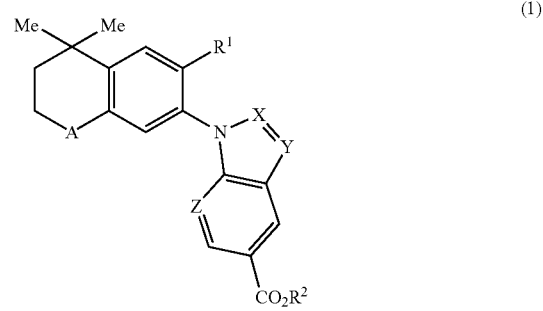

(1)

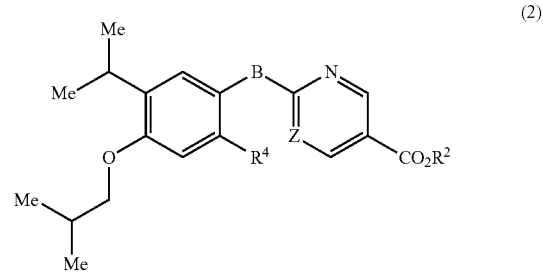

(2)

5 Claims, 4 Drawing Sheets

(56) References Cited

FOREIGN PATENT DOCUMENTS

WO    WO 2013/020966 A1    2/2013
WO    WO 2013/090616 A1    6/2013

OTHER PUBLICATIONS

Fuminori Ohsawa, et al., "Mechanism of Retinoid X Receptor Partial Agonistic Action of 1-(3,5,5,8,8-Pentamethyl-5,6,7,8-tetrahydro-2-naphthyl)-1H-benzotriazole-5-carboxylic Acid and Structural Development to Increase Potency", Journal of Medicinal Chemistry, 2013, pp. 1865-1877, vol. 56.
International Search Report (PCT/ISA/210) dated Jul. 5, 2016, by the Japanese Patent Office as the International Searching Authority for International Application No. PCT/JP2016/060714.
Written Opinion (PCT/ISA/237) dated Jul. 5, 2016, by the Japanese Patent Office as the International Searching Authority for International Application No. PCT/JP2016/060714.

[Fig. 1]
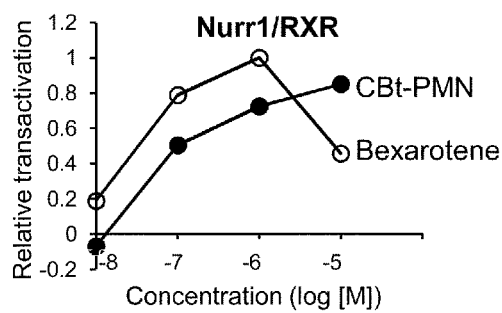
[Fig. 2]
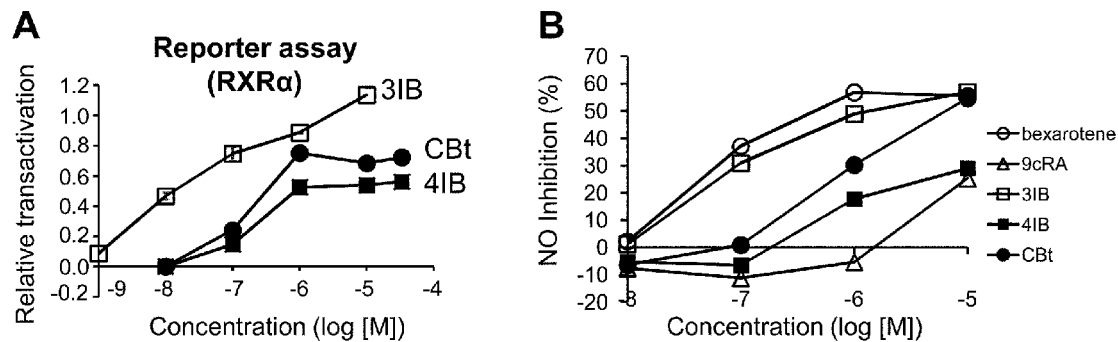

[Fig. 3]
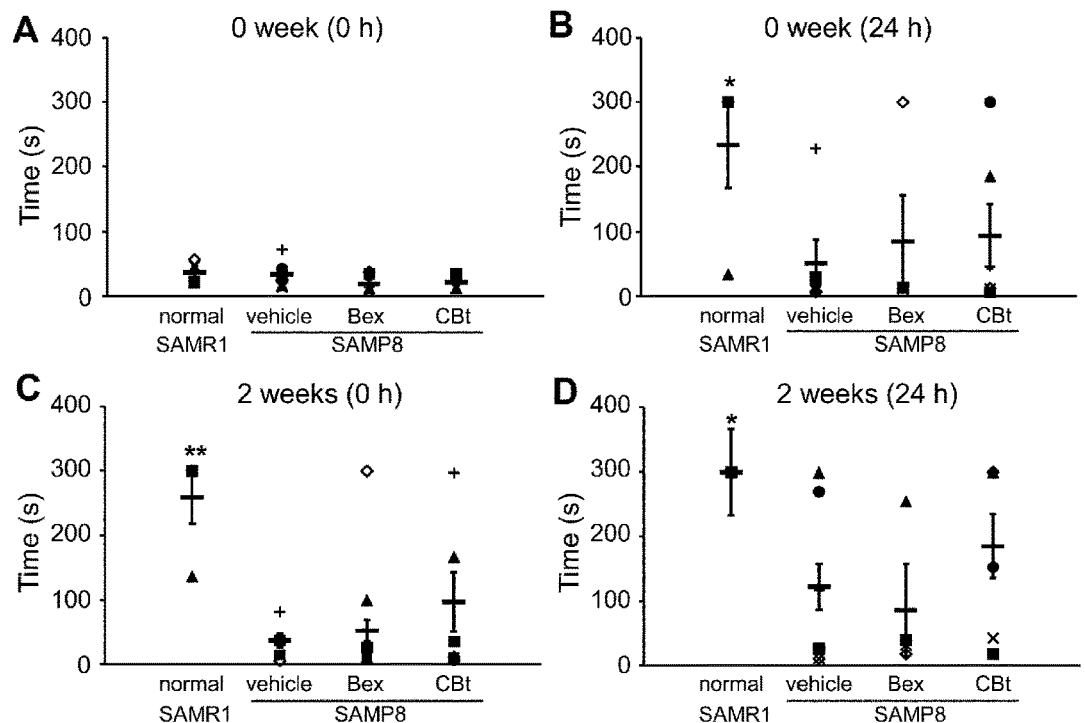
[Fig. 4]
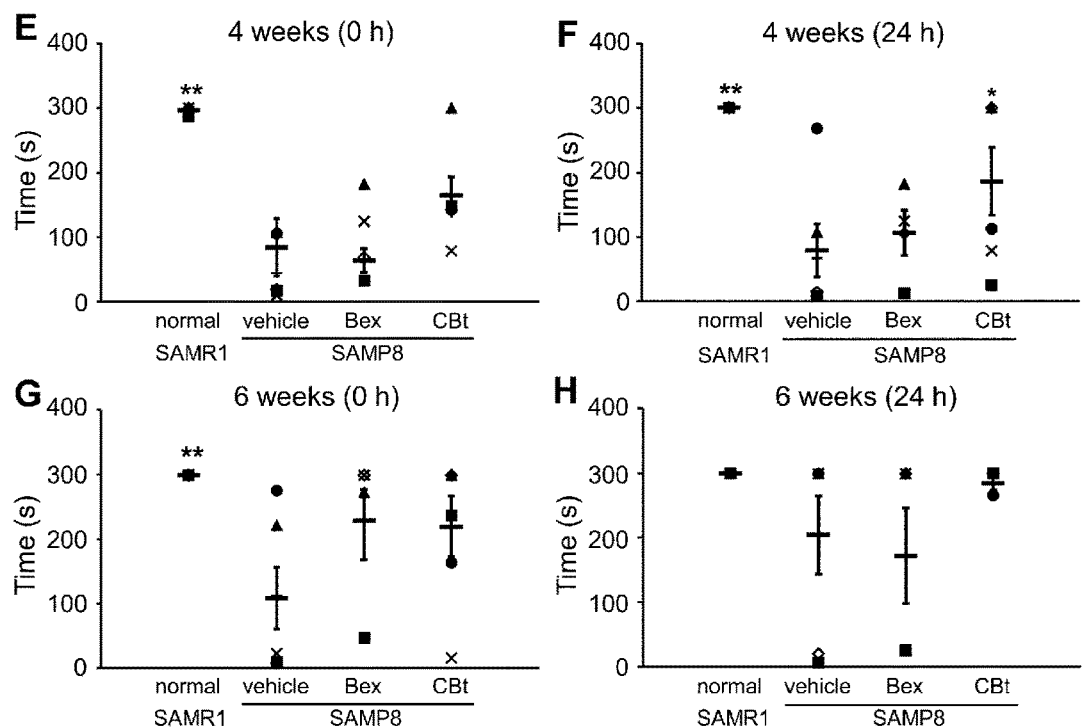

[Fig. 5]
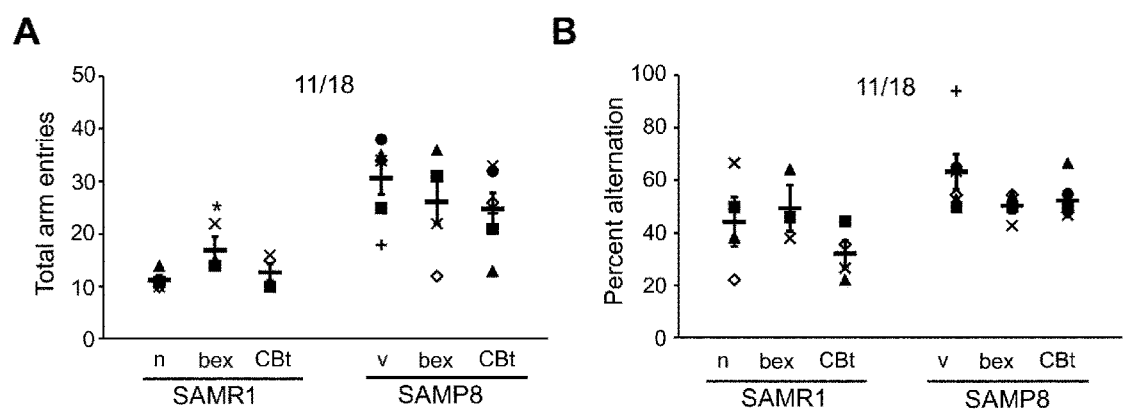
[Fig. 6]
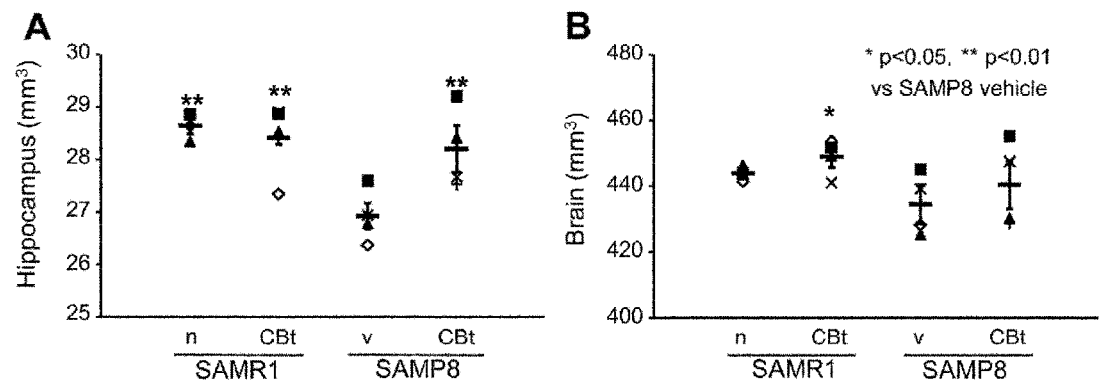

[Fig. 7]
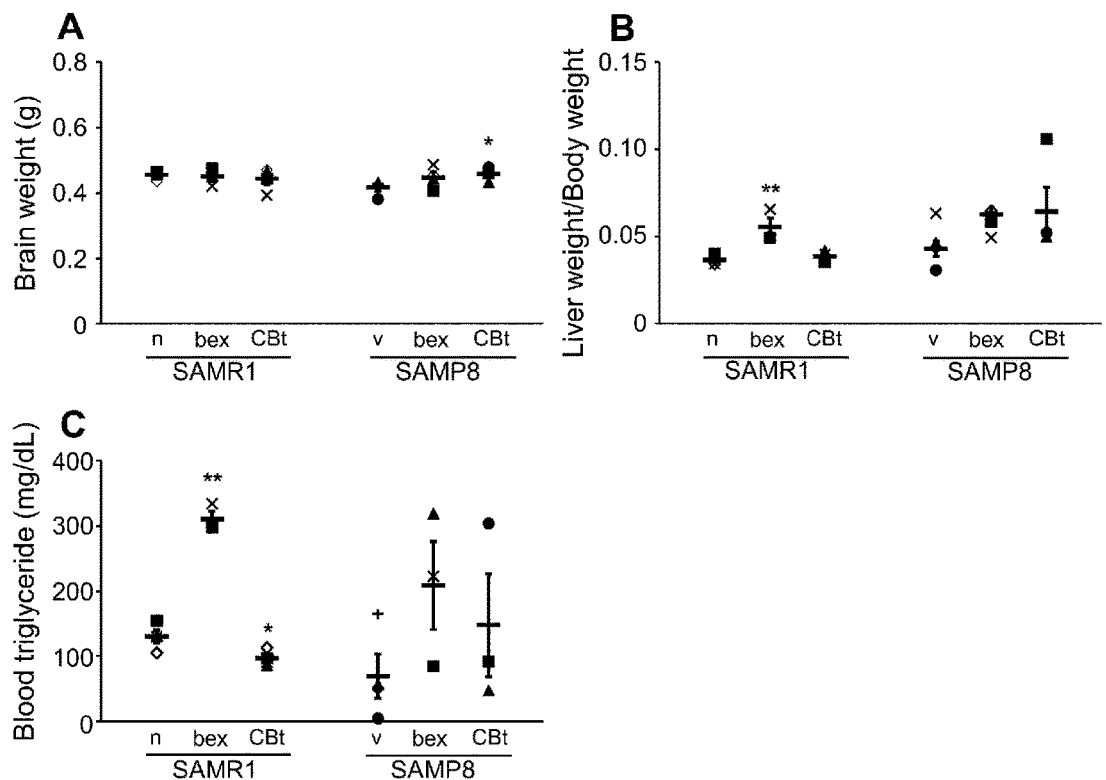
[Fig. 8]
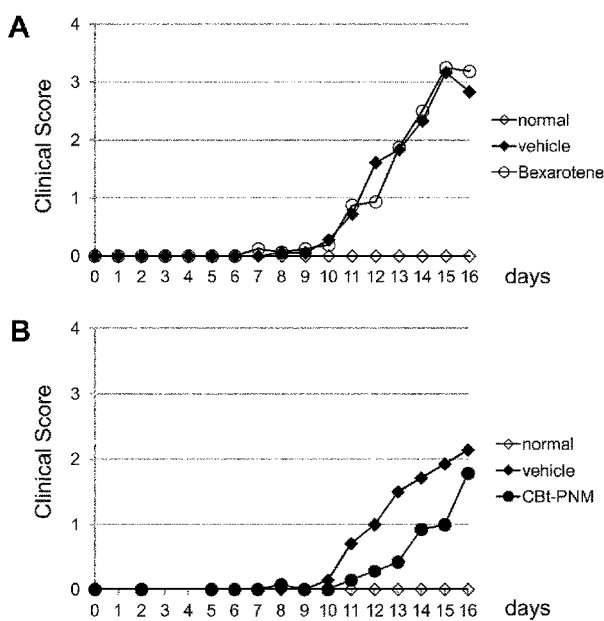

PHARMACEUTICAL COMPOSITION FOR TREATMENT OR PREVENTION OF NEURODEGENERATIVE DISEASES

TECHNICAL FIELD

The present invention relates to a pharmaceutical composition for treating or preventing a neurodegenerative disease comprising an RXR agonist as an active ingredient.

BACKGROUND ART

There have been studies on a strategy for treating neurodegenerative diseases, in particular dementia (including Alzheimer's disease), where a nuclear receptor is targeted. For example, an agonist to a PPAR (peroxisome proliferator-activated receptor) has been described to be effective for treating dementia. It has been described that bexarotene which is a full agonist targeting a retinoid X receptor (RXR) is effective for treating dementia.

Bexarotene has been used a therapeutic agent for cutaneous invasive T-cell lymphoma in many countries including the United States and Japan, and has been reported to have an effect for treating type II diabetes, a therapeutic effect in an Alzheimer's disease model mouse and an effect for treating Parkinson's disease. However, conventional RXR agonists including bexarotene have a problem of side effects such as decreased thyroid activity, enlargement of the liver, weight gain and elevation of blood triglyceride level. Any RXR agonist having such a problem of side effects is a full agonist which can fully activate a RXR.

We have hypothesized that there is a difference between a threshold of drug efficacy by an RXR agonist and a threshold of expression of side effects such as enlargement of the liver. We have further supposed that a partial agonist whose activation ability (efficacy) is reduced in comparison with an RXR full agonist could exhibit drug efficacy capable of improving not only insulin resistance but also glucose tolerance as a sole drug while avoiding side effects. As a result of study, we have found that RXR partial agonists which we have created exhibit potent antihyperglycemic action and improvement in insulin resistance while reducing side effects as a conventional problem associated with an RXR full agonist. Molecular structures of typical RXR partial agonists which we have created are as follows (see Patent Reference Nos. 1 to 4).

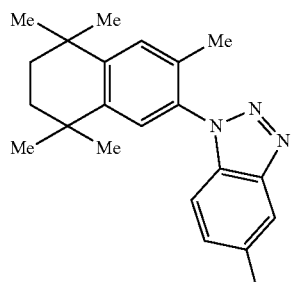

CBt-PMN

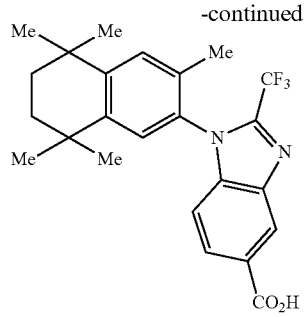

CBTF-PMN

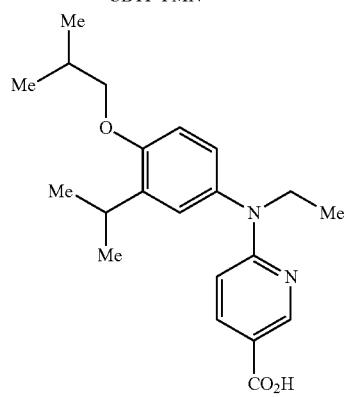

NEt-4IB

Each of these compounds was orally administered to mice at a dose of 30 mg/kg/day for one week, and body weight change over a week and also enlargement of the liver and elevation of blood triglyceride level as a problem for an RXR full agonist were determined. As a result, tendency to weight gain was not observed in groups treated with CBt-PMN or NEt-4IB as an RXR partial agonist. Furthermore, for a liver weight and a triglyceride level, there was not a difference between the CBt-PMN or NEt-4IB group and a vehicle group. Furthermore, although these compounds were orally repeatedly administered to male and female rats at a dose of 30 mg/kg/day repeatedly for 28 days, no significant differences in weight change, water intake and food intake were observed, compared with a vehicle treatment group (see Non-patent Reference Nos. 1 to 3).

PRIOR ART REFERENCES

Patent References

Patent Reference No. 1: JP 2010-111588A
Patent Reference No. 2: JP 2013-177329A
Patent Reference No. 3: WO 2008/105386
Patent Reference No. 4: JP 2014-076953

Non-Patent References

Non-patent Reference No. 1: H. Kakuta et al., ACS Med. Chem. Lett. 3, 427-432 (2012)
Non-patent Reference No. 2: F. Ohsawa et al., J. Med. Chem. 56, 1865-1877 (2013)
Non-patent Reference No. 3: K. Kawata et al., J. Med. Chem. 58, 912-926 (2015)

SUMMARY OF THE INVENTION

Problems to be Solved by the Invention

It is known that an RXR agonist alone activate RXR heterodimers such as PPAR/RXR, LXR/RXR, and Nurr1/RXR which reportedly has neuroprotective action (permissive mechanism). It is furthermore known that RXR agonists with different structures have different ability of activating an RXR permissive heterodimer by an RXR agonist alone, even though these have comparable RXR activating ability. Therefore, even when bexarotene and so on which is an RXR full agonist is therapeutically effective against Alzheimer's disease and Parkinson's disease, it cannot be judged that an RXR partial agonist is also effective. Furthermore, it cannot be determined that a partial agonist with reduced ability of activating an RXR exhibits reduction in desired efficacy, compared to an RXR full agonist.

Furthermore, in order to be therapeutically effective against diseases in brain or central-nerve diseases such as Alzheimer's disease and Parkinson's disease, a drug must be brain-migratable. However, brain-migration ability cannot be easily predicted.

Means for Solving the Problems

After intense investigation, we have found that RXR partial agonists such as CBt-PMN and NEt-4IB have therapeutic effects against neurodegenerative diseases over bexarotene, to achieve this invention. Specifically, the present invention relates to a pharmaceutical composition for treating or preventing a neurodegenerative disease comprising an RXR partial agonist as an active ingredient.

The present invention provides a pharmaceutical composition for treating or preventing a neurodegenerative disease, comprising an RXR agonist as an active ingredient which is a compound represented by formula (1) or (2):

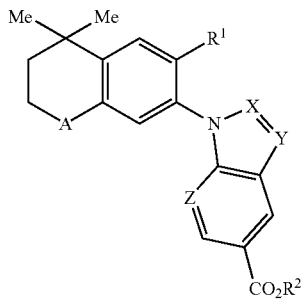

(1)

wherein A represents $CMe_2$, N-methyl, N-ethyl or N-isopropyl; X represents N, CH or C—$CF_3$; Y and Z represent N or CH; $R^1$ represents methyl, hydroxy, methoxy or ethoxy; and $R^2$ represents H, methyl or ethyl;

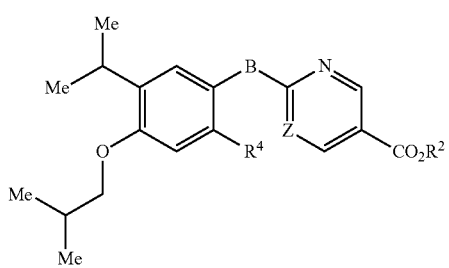

(2)

wherein B represents $NR^3$ or $CHR^3$; $R^3$ represents alkyl; $R^4$ represents H, halogen, alkyl, alkenyl, aryl, alkynyl, alkoxy or acyl; and Z and $R^2$ are as defined for formula (1).

Here, it is preferable that the RXR agonist is effective in inhibiting production of nitric oxide. It is also preferable that the RXR agonist has Nurr1/RXR activating effect. It is also preferable that the RXR agonist is effective in ameliorating a learning/memory disorder. It is also preferable that the RXR agonist is effective in ameliorating cerebral atrophy. In a suitable embodiment, the neurodegenerative disease is dementia, Parkinson's disease or multiple sclerosis.

Effects of the Invention

A pharmaceutical composition for treating or preventing a neurodegenerative disease of the present invention reduces elevation of triglyceride level observed in bexarotene as an existing RXR full agonist and is expected to be more effective than bexarotene in treatment of a neurodegenerative disease and in prevention of the disease by inhibiting progression thereof. Thus, the composition can be utilized as a medicine for such a disease.

A pharmaceutical composition for treating or preventing a neurodegenerative disease of the present invention expresses neuroprotective action by activating Nurr1 (nuclear receptor related 1 protein)/RXR, and can treat or prevent other diseases mainly caused by an inflammatory substance such as nitric oxide, via proper activation of an RXR. Therefore, there can be provided a pharmaceutical composition which is effective against diseases including stroke; ischemic damage to a nerve system; neurotraumas such as blow-induced brain damage, spinal cord damage and traumatic damage to a nerve system; multiple sclerosis and other immune-mediated neurological disorders; and bacterial and viral meningitis.

BRIEF DESCRIPTION OF THE DRAWINGS

FIG. 1 shows effects of an RXR partial agonist on Nurr1/RXR in Example 1.

FIG. 2 shows inhibition activity of an RXR partial agonist to nitric oxide production by macrophage induced by LPS stimulation in Example 2.

FIG. 3 shows effects of administration of an RXR partial agonist on a senescence-accelerated mouse (SAMP8) in Example 4 (0 to 2 week step-through test).

FIG. 4 shows effects of administration of an RXR partial agonist on a senescence-accelerated mouse (SAMP8) in Example 4 (4 to 6 week step-through test).

FIG. 5 shows effects of administration of an RXR partial agonist on a senescence-accelerated mouse (SAMP8) in Example 5 (Y-maze test).

FIG. 6 shows variation in a brain and a hippocampus volumes of a senescence-accelerated mouse (SAMP8) by administration of an RXR partial agonist in Example 6.

FIG. 7 shows variation in blood data and a liver weight of a senescence-accelerated mouse (SAMP8) by administration of an RXR partial agonist in Example 7.

FIG. 8 shows effects of administration of an RXR partial agonist on a pathological score of a multiple sclerosis model mouse in Example 9.

MODES FOR CARRYING OUT THE INVENTION

The present invention relates to a pharmaceutical composition comprising a partial agonist to a retinoid X receptor (RXR) which is a nuclear receptor, for treating or preventing neurodegenerative diseases, particularly dementia (including Alzheimer's disease), Parkinson's disease, multiple sclerosis and neurological diseases caused by an inflammatory component. A pharmaceutical composition of the present invention comprises an RXR partial agonist as an active ingredient.

A pharmaceutical composition for treating or preventing a neurodegenerative disease of the present invention comprises a compound represented by formula (1) or (2) which is an RXR agonist, as an active ingredient.

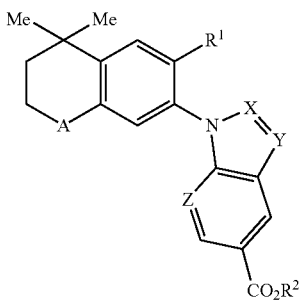

(1)

wherein A represents $CMe_2$, N-methyl, N-ethyl or N-isopropyl; X represents N, CH or C—$CF_3$; Y and Z represent N or CH; $R^1$ represents methyl, hydroxy, methoxy or ethoxy; and $R^2$ represents H, methyl or ethyl;

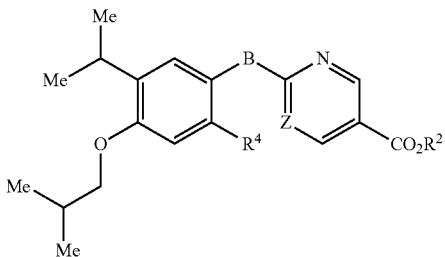

(2)

wherein B represents $NR^3$ or $CHR^3$; $R^3$ represents alkyl; $R^4$ represents H, halogen, alkyl, alkenyl, aryl, alkynyl, alkoxy or acyl; and Z and $R^2$ are as defined for formula (1).

The compound represented by formula (1) or (2) can be a pharmaceutically acceptable salt. If there can be isomers of the compound (for example, optical isomers, geometric isomers or tautomers), the compound embraces these isomers. The compound also embraces solvates and hydrates, and various shapes of crystals.

In the present invention, pharmaceutically acceptable salts include pharmacologically and pharmaceutically acceptable common salts. The following are specific examples of such salts.

Examples of a base addition salt include alkali metal salts such as sodium salts and potassium salts; alkaline earth metal salts such as calcium salts and magnesium salts; ammonium salts; aliphatic amine salts such as trimethylamine salts, triethylamine salts, dicyclohexylamine salts, ethanolamine salts, diethanolamine salts, triethanolamine salts and procaine salts; aralkylamine salts such as N,N-dibenzylethylenediamine salts; heteroaromatic amine salts such as pyridine salts, picoline salts, quinoline salts and isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts and tetrabutylammonium salts; and basic amino acid salts such as arginine salts and lysine salts.

Examples of an acid addition salt include inorganic acid salts such as hydrochlorates, sulfates, nitrates, phosphates, carbonates, bicarbonates and perchlorates; organic acid salts such as acetates, propionates, lactates, maleates, fumarates, tartrates, malates, citrates and ascorbates; sulfonates such as methanesulfonates, isethionates, benzenesulfonates and p-toluenesulfonates; and acidic amino acid salts such as aspartates and glutamates.

In formula (1), A represents $CMe_2$, N-methyl, N-ethyl or N-isopropyl, particularly preferably $CMe_2$. X represents N, CH or C—$CF_3$, particularly preferably N. Y represents N or CH, particularly preferably N. Z represents N or CH, particularly preferably CH. $R^1$ represents methyl, hydroxy, methoxy or ethoxy, particularly preferably methyl. $R^2$ represents H, methyl or ethyl, particularly preferably H.

In formula (2), B represents $NR^3$ or $CHR^3$, preferably $NR^3$. $R^3$ represents alkyl. The term "alkyl" as used herein means a straight-chain, branched or cyclic alkyl group having 1 to 20, preferably 1 to 10 carbon atoms including methyl, ethyl, n-propyl, isopropyl, n-butyl, isobutyl, sec-butyl, tert-butyl, n-pentyl, isopentyl, neopentyl, tert-pentyl, n-hexyl, isohexyl, n-heptyl, n-octyl, n-nonyl and n-decyl; more preferably an alkyl group having 1 to 6 carbon atoms including methyl, ethyl, n-propyl, isopropyl, n-butyl, isobutyl, sec-butyl, tert-butyl, n-pentyl, isopentyl, neopentyl, tert-pentyl, n-hexyl and isohexyl, particularly preferably ethyl.

In formula (2), $R^4$ represents H, halogen, alkyl, alkenyl, aryl, alkynyl, alkoxy or acyl, particularly preferably H. The alkyl can be as defined for $R^3$.

Alkenyl in $R^4$ means a straight-chain or branched alkenyl having 2 to 20, preferably 2 to 8 carbon atoms where the above alkyl structure contains one or more double bonds, including vinyl, 1-propenyl, 2-propenyl, 1-butenyl, 2-butenyl, 3-butenyl, 1,3-butadienyl and 3-methyl-2-butenyl.

Aryl in $R^4$ means a monocyclic aromatic hydrocarbon group (phenyl) and a polycyclic aromatic hydrocarbon group (for example, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl), preferably phenyl or naphthyl (1-naphthyl, 2-naphthyl).

Alkynyl in $R^4$ means an alkynyl having 2 to 20, preferably 2 to 10 carbon atoms where the above alkyl structure contains one or more triple bonds, including ethynyl, 1-propynyl, 2-propynyl, 1-butynyl, 2-butynyl and 3-butynyl.

Alkoxy in $R^4$ means a straight-chain or branched alkoxy group having 1 to 20 carbon atoms, including a methoxy group, an ethoxy group, a propoxy group, an isopropoxy group, a butoxy group, an isobutoxy group, a sec-butoxy group, a tert-butoxy group, a pentyloxy group, a hexyloxy group, an octadecanoxy group and an aryloxy group. It is preferably a straight-chain or branched lower alkoxy group having 1 to 6 carbon atoms.

Acyl in $R^4$ means alkanoyl, aroyl or the like. An example of the alkanoyl is alkanoyl having an alkyl group having 1 to 6, preferably 1 to 4 carbon atoms (formyl, acetyl, trifluoroacetyl, propionyl, butyryl and so on). An example of the aroyl is an aroyl group having 7 to 15 carbon atoms, including benzoyl and naphthoyl.

Z and $R^2$ in formula (2) are as defined for formula (1).

The compound represented by formula (1) or (2) have partial agonist activity to an RXR. Since an RXR is here a nuclear receptor involving DNA transcription, the compound represented by formula (1) or (2) can be referred to as a "transcriptional regulatory compound". The term, "regulatory" or its synonym as used herein, must be interpreted as broad as possible, including enhancement or inhibition of an action. Whether a compound of the present invention has enhancing or inhibiting action can be easily tested by a method specifically described in Experimental section in this specification.

There are no particular restrictions to a dosage of a pharmaceutical composition of the present invention. A dosage can be appropriately determined in any dosage regimen, for example, when action of a retinoid is regulated by using a compound of the present invention in combination with a medical drug containing a retinoid such as retinoic acid and tamibarotene which is reportedly effective against dementia, as an active ingredient, or when, without combining a retinoid-containing medical drug, a drug of the present invention is administered for regulating action of retionic acid existing in a living organism. For example, for oral administration, an active ingredient can be used within a range of about 0.01 to 1000 mg per day for an adult. When a medicine containing a retinoid as an active ingredient is used in combination with a drug of the present invention, the drug of the present invention can be administered during, and/or either before or after administrating the retinoid.

In terms of a pharmaceutical composition of the present invention, one or two or more compounds selected from compounds represented by formula (1) or (2) can be administered directly, but can be preferably administered as an oral or parenteral pharmaceutical composition containing one or two or more of the compounds described above. An oral or parenteral pharmaceutical composition can be produced using formulation additives available for the person skilled in the art, that is, pharmacologically and pharmaceutically acceptable carriers. Alternatively, one or two or more of the compounds represented by formula (1) or (2) are added to another pharmaceutical composition effective for treating a neurodegenerative disease, that is, they can be used as a pharmaceutical composition in the form of so-called combination drug. Specifically, combination with a cholinesterase inhibitor such as donepezil hydrochloride or an NMDA receptor inhibitor such as memantine hydrochloride can be used for dementia. Combination with a dopaminergic precursor such as levodopa, a dopamine receptor agonist, a selective monoamine oxidase B inhibitor, a COMT inhibitor or a muscarinic antagonist can be used for Parkinson's disease.

A pharmaceutical composition suitable for oral administration can be, for example, tablet, capsule, powder, fine granules, granules, liquid and syrup. A pharmaceutical composition suitable for parenteral administration can be, for example, injection, infusion, suppository, inhalant, eye drop, nasal drop, ointment, cream and patch. Pharmacologically and pharmaceutically acceptable carriers used for preparing the pharmaceutical composition include an excipient, a disintegrant or disintegration aid, a binder, a lubricant, a coating agent, a colorant, a diluent, a base, a dissolving agent or dissolution aid, a tonicity agent, a pH modifier, a stabilizer, a propellant and an adhesive.

A pharmaceutical composition of the present invention is used as a pharmaceutical composition for treating or preventing a neurodegenerative disease. A compound represented by formula (1) or (2) contained in a pharmaceutical composition of the present invention is an RXR agonist, which is not a full agonist, but a partial agonist with reduced activating ability (efficacy). An RXR partial agonist as an active ingredient can improve therapeutic or preventive effect while reducing side effects.

In a pharmaceutical composition of the present invention, the RXR agonist preferably has the effect of inhibiting nitric oxide production. Furthermore, the RXR agonist preferably has the effect of activating Nurr1/RXR, and also preferably has the effect of ameliorating a learning/memory disorder. In addition, the RXR agonist preferably has the effect of ameliorating cerebral atrophy.

A pharmaceutical composition for treating or preventing a neurodegenerative disease of the present invention expresses neuroprotective action by activating Nurr1/RXR, and can treat or prevent other diseases mainly caused by an inflammatory substance such as nitric oxide, via proper activation of an RXR. Therefore, there can be provided a pharmaceutical composition which is effective against diseases including stroke; ischemic damage to a nerve system; neurotraumas such as blow-induced brain damage, spinal cord damage and traumatic damage to a nerve system; multiple sclerosis and other immune-mediated neurological disorders; and bacterial and viral meningitis. In a preferable embodiment, the neurodegenerative disease is dementia, Parkinson's disease or multiple sclerosis.

EXAMPLES

There will be specifically described various pharmacological actions of the compound represented by formula (1) or (2) and production processes therefor. Any compound encompassed within the scope of the present invention can be produced by appropriately modifying or changing starting materials and reagents, and the reaction conditions used in the process for producing each compound. The present invention is, however, not limited to the scope of the following examples. The following experiments were performed under the approval of the Animal Care and Use Committee, Okayama University.

Example 1

<Activation of an Nurr1/RXR Heterodimer by an RXR Agonist>
(1) Objective

It is known that activation of Nurr1/RXR is effective for protection of dopamine nerve, and Nurr1/RXR is a permissive heterodimer which can be activated by an RXR agonist alone. Thus, the presence of activation of Nurr1/RXR by various RXR agonists was studied.

(2) Measurement Principle

Many of nuclear receptors are transcription factors involving transcription control. Therefore, a reporter gene assay is conducted as means for determining its transcription activity. An RXR receptor protein expression plasmid and a reporter plasmid are transduced into a cell such as a COS-1 cell and a HeLa cell, to overexpress a fusion protein. Here, when an RXR agonistic substance (ligand) is bound to a receptor, transcription ligand-dependently occurs, so that a downstream fusion protein is formed, leading to initiation of production of a downstream luciferase. By measuring activity of the luciferase, RXR agonistic activity was determined. For heterodimer assay with Nurr1, an expression plasmid of Nurr1 and a reporter plasmid having a gene sequence corresponding to Nurr1 were transduced. Furthermore, a secreted alkaline phosphatase (SEAP) expression plasmid was transduced, and activity of the SEAP was determined for correction of a transformation efficiency.

(3) Cultivation of Host Cells

Dulbecco's modified Eagle's MEM medium (DMEM) was used as a cell growth medium. First, in 500 mL of ultrapure water (produced by Milli-Q®) was dissolved 4.75 g of DMEM powder, and the solution was sterilized by autoclaving (121° C., 20 minutes). After cooling to room temperature, to the solution was added inactivated fetal bovine serum (FBS) to 10% (v/v), and then 10 mL of autoclave sterilized 10% $NaHCO_3$ was added. Then, 0.292 g of L-glutamine dissolved in 8 mL of ultrapure water which had been sterilized by filtration was added, to prepare a culture medium.

Subculturing of each cell was conducted as follows. A culture supernatant of cells cultured on a 100 mm culture dish was removed, and then trypsinized to harvest the cells, which were then centrifuged at 4° C. and 1000 rpm for 3 minutes, and a growth medium was added to disperse the cells. Subsequently, to a 100 mm culture dish was added 15 mL of the growth medium containing the dispersed cells, which was then cultured at 37° C. in the presence of 5% $CO_2$.

Transformation was conducted using Effectene™ Transection Reagent (from QIAGEN Inc.). Bexarotene (bexarotene) was used as a positive control for an RXR. These were dissolved in DMSO to prepare a stock solution, which was measured in an assay plate.

(4) Determination of Transcription Activity (Day 1) In 60 mm culture dish, $50 \times 10^4$ COS-1 cells with 5 mL of a growth medium were inoculated and cultured overnight.

(Day 2) By lipofection using Effectene® Transection Reagent (QIAGEN Inc.), RXR expression plasmid pCMX-RXRα (0.5 μg), Nurr1 expression plasmid pCMX-Nurr1 (0.5 μg), Nurr1 response luciferase reporter plasmid NX' 3× 3-tk-Luc (4 μg) and SEAP (1 μg) were transduced. These plasmids were provided by Professor Makishima, Nippon University.

(Day 3) After 16 to 18 hours, a culture supernatant was removed, and then trypsinized to harvest the cells, which were then centrifuged at 4° C. and 1000 rpm for 3 minutes, and a growth medium was added to disperse the cells. The cells were inoculated into a 96-well white plate to $20 \times 10^4$ cells/well. Then, each compound was added such that a DMSO concentration is less than 1%.

(Day 4) After 24 hours, 25 μL of the supernatant was used for SEAP measurement while the remaining cell liquid was used for determining luciferase activity.

SEAP measurement was performed in accordance with a method described in Methods in molecular biology, 63, pp. 49-60, 1997/BD Great EscAPe SEAP User manual (BD bioscience).

These measurements were conducted by the following method. To 25 μL of the 4-day supernatant was added 25 μL of the dilution buffer solution, and the mixture was incubated at 65° C. for 30 minutes. Then, after cooling the mixture to room temperature, to the mixture were added an assay buffer solution (7 μL), 10×MUP (0.3 μL) and a dilution buffer solution (2.7 μL), and the mixture was incubated at room temperature in the dark for 60 minutes. Then, using a microplate reader (Infinite™ 200, TECAN Group Ltd.), a fluorescence intensity was determined at an excitation wavelength of 360 nm and at a fluorescence wavelength of 465 nm.

The assay buffer solution was prepared by the following method. L-homoarginine (0.45 g) and magnesium chloride (0.02 g) were dissolved in 50 mL of ultrapure water (produced by Milli-Q®), and diethanolamine (21 mL) was added to the solution. After the pH was adjusted to 9.8 using hydrochloric acid, ultrapure water was added until the total amount was to be 100 mL, and the solution was stored at 4° C.

The dilution buffer solution was prepared by the following method. In 90 mL of ultrapure water (produced by Milli-Q®) were dissolved sodium chloride (4.38 g) and Tris Base (2.42 g). Then, the pH was adjusted to 7.2 using hydrochloric acid, to prepare a 5× concentration dilution buffer solution, which was then stored at 4° C. By 5-fold diluting the solution immediately before the use, a dilution buffer solution was prepared.

4-Methylumbelliferyl phosphate (MUP) was dissolved in ultrapure water (produced by Milli-Q®) to 25 mM, and the solution was stored at −20° C. as 10×MUP.

Luciferase activity was determined by measuring, using a 96-well white plate (from NUNC Company), a luminescent intensity of reaction product with a luminescence substrate (Steady-Glo® Luciferase Assay System, Promega Corporation) by a microplate reader (Infinite™ 200, TECAN Group Ltd.).

(5) Measurement Results

The results of the above measurement are shown in FIG. 1. The measurement results were obtained as a relative activity where 100% was transcription activity when 1 μM bexarotene as a positive control was reacted. Consequently, Nurr1/RXR transcription activity was observed for CBt-PMN.

Example 2

<Inhibition Activity of an RXR Partial Agonist on Macrophage Nitric Oxide Production by LPS Stimulation>

(1) Objective

Expression of an inflammatory cytokine such as iNOS (inducible nitric oxide synthase) and TNFα (tumor necrosis factor-α) is often induced by activation of NFκB as a transcription factor. Activation of NFκB involves a transcriptional coupling factor which is called as a coactivator. When an RXR is activated by an agonist, the RXR also induces a coactivator. It has been described that activated PPARγ captures a coactivator used for activating NFκB, resulting in anti-inflammatory effect. Thus, an RXR is expected to have a similar effect.

Raw264.7 cells which are murine macrophage-like cells express iNOS involving activation of NFκB by a lipopolysaccharide (LPS) known as a ligand for TLR-4, to produce nitric oxide (NO). When a steroidal anti-inflammatory drug such as predonisolone is added to the system, inhibition of iNOS expression and NO production is observed by capturing a coactivator from NFκB by activated glucocorticoid receptor (GR). Thus, various RXR agonists were studied for their ability of inhibiting NO production in a system using Raw264.7 cells and LPS.

(2) Method for Determining NO (Day 1) In a 96-well plate, Raw264.7 cells were inoculated at $1.0 \times 10^5$ cells/well.

(Day 2) After adding LPS (100 ng/mL) and each RXR agonist as a DMSO solution (final concentration: 0.1%), the culture was incubated for 48 hours.

(Day 4) Using 50 μL of the culture supernatant, an NO concentration was determined by Griess method (utilizing PROMEGA G2930).

(3) Results

The results are shown in FIG. 2. In this figure, "A" is RXR activation ability of 3IB (NEt-3IB: RXR full agonist), 4IB (NEt-4IB: RXR partial agonist), and CBt (CBt-PMN: RXR partial agonist), while "B" is NO-production inhibition ability of each RXR agonist when Raw264.7 cells are stimulated by LPS. It is found that CBt-PMN at a concentration of 10 μM produces NO at a level comparable to bexarotene. Here, NEt-3IB is a compound corresponding to NEt-4IB with the positions of isopropyl and isobutoxy being interchanged. Here, 9cRA is 9-cis-retinoic acid.

Example 3

<Brain-Migration Ability of an RXR Partial Agonist>
(1) Objective

To confirm that monitoring a brain concentration of an administered drug is sufficiently effective for showing drug efficacy, taking properties of a targeted disease into consideration.

(2) Method for Administering a Compound

A compound was administered at a dose of 30 mg/kg mouse body weight. A compound to be administered was prepared by dissolving it in a 1% final concentration of ethanol and suspending the solution in a 0.5% carboxymethyl cellulose (CMC) solution. Animals subjected to administration were male ICR mice (6 week old), and they were fasted from 17 o'clock the day before.

(3) Preparation of a Sample for Measuring a Plasma Concentration

Blood was collected from an inferior vena cava of a mouse under ether anesthesia, and then the brain was removed from the mouse. The collected blood was put in a heparinized tube, mixed with inversion and then centrifuged (600 g) for 5 minutes to obtain plasma. To 100 μL of the plasma were added 100 μL of an ammonium acetate buffer solution and 1 mL of ethyl acetate, and the mixture was stirred by a vortex mixer for 30 seconds and then left at room temperature for 10 minutes. Then, the mixture was centrifuged 30 seconds and 800 μL of the supernatant was concentrated by a centrifugal evaporator. To the concentrate was added 100 μL of an HPLC eluent to prepare an HPLC sample.

(4) Preparation of a Sample for Measuring a Cerebral Concentration

Under ether anesthesia, the brain was removed from a mouse after administrating a drug, and about 100 mg of the brain was weighed into a 2 mL Eppendorf tube. After adding 1000 μL of methanol per 100 mg of the brain, the mixture was homogenized. After the homogenization, the homogenate was centrifuged at 10,000 g at 10 to 15° C. for 10 minutes. Then, in a separate 1.5 mL Eppendorf tube, 700 μL of the supernatant ethanol was dispensed and concentrated to dryness by a centrifugal evaporator. To the concentrate was added 70 μL of the HPLC eluent, to give a solution (10× concentrate).

(5) Assay Using HPLC

A 30 μM solution of the drug in methanol was prepared and diluted with the HPLC eluent (5 mM $AcONH_4$, pH5, MeOH) to 10, 3, 1 and 0.3 μM. Using these, a calibration curve was formed. The plasma and the blood samples were subjected to measurement and a measured value was converted to a concentration.

(6) Results

The results are shown in the table below.

TABLE 1

| Blood and cerebral concentrations one hour after 30 mg/kg single-dose administration (ave ± SEM) | | |
|---|---|---|
| | Plasma (μM) | Brain (μM) |
| Bexarotene | 11.9 ± 2.5 | 5.6 ± 1.2 |
| CBt-PMN | 15.8 ± 6.0 | 11.4 ± 3.7 |

As shown in the table, CBt-PMN migrates more smoothly to the brain than bexarotene.

Example 4

<Effects of Administration of an RXR Partial Agonist on a Senescence-Accelerated Mouse (SAMP8) (Step-Through Test)>
(1) Objective From inquiry to Japan SLC Inc. which is a supplier of SAMP8 mice, it has found that cognitive ability of SAMP8 mice is evaluated by a step-through test. Thus, the test procedure was used for evaluating cognitive ability improvement by administrating an RXR partial agonist.

(2) Housing of Mice

After joining the SAM Council, four 4-week old male SAMP mice were purchased from SHIMIZU Laboratory Supplies Co., Ltd. In each cage, one mouse was housed to 14 month to 16 month old with having free access to MF feed and water.

(3) Dosing to Mice

From the study initiation day, mice were dosed with MF feed from Oriental Yeast Co., Ltd., which contained each drug in 0.015%. A ration per day was 5 to 10 g on average, which corresponds to a dosage per kg body weight per day: 15 to 30 mg/kg/day.

(4) Step-Through Test
[Instruments]

A step-through test system from Muromachi Kikai Co., Ltd. (for mouse: mouse cage STC-001M) was used. This system consists a light compartment with a ceiling light and a shaded dark compartment and a door connecting these compartments, where the floor of the dark compartment is equipped with electric cables for electric stimulation. Electric stimulation was generated using a shock generator SGS-003DX (Muromachi Kikai Co., Ltd.).
[Training Trial]

A mouse was placed in a closed light chamber and after 20 seconds, the door was opened to allow the mouse to move to the dark chamber which the animal favors. After the mouse moved to the dark chamber, the door was closed followed by electric stimulation (0.3 mA, 3 seconds). Then, the mouse was returned to a common breeding environment and housed.
[Retention Trial]

A certain time after the training trial (after 10 minutes, 1 hour, 24 hours), the mouse was again placed in the light chamber and a time until the mouse moved to the dark chamber was recorded as a response latency. The response latency was measured by a stopwatch. A longer response latency is judged that the animal remembers an aversive stimulus.
[Light-Place Residence Time]

Here, 300 seconds was to maximum.

The mice used were as follows.

SAMR1: normal (n=4), bexarotene (n=3), CBt-PMN (n=4)

SAMP8: vehicle (n=6), bexarotene (n=4), CBt-PMN (n=6)

(5) Results

The results are shown in FIGS. 3 and 4. Each marker in the figures indicates each mouse (individual). Three to six mice per one group were used.

In the initial test (A), it can be seen that all mice immediately moved to the dark chamber. In the test after 24 hours (B), a response latency was 200 seconds on average in normal mice ("normal" in SAMR1) having memory and cognitive ability. In contrast, SAMP8 mice including a drug administration group have declined memory and cognitive ability and thus a response latency was less than 100 seconds on average.

In the tests after 2 weeks (C and D), a response latency was prolonged only in SAMR1, while the SAMP8 group gave results comparable to the initial test. However, in the tests 4 weeks after drug administration (E, F, G, H), a response latency was prolonged only in a vehicle group (non-administration group) among SAMP8 mice receiving CBt-PMN.

Example 5

<Effects of Administration of an RXR Partial Agonist on a Senescence-Accelerated Mouse (SAMP8) (Y-Maze Test)>

(1) Objective and Mice Used

In this test, the mice used in the step-through test were used as they were. That is because an objective of this test is to determine whether prolongation of a response latency of the mice in the step-through test is due to behavioral suppression of the mice by drug administration.

(2) Y-Maze Test

After the step-through test, a Y-maze for a mouse (arm length: 40 cm) was used and mice were allowed to freely move for 8 minutes. In a Y-shaped system, a near-side arm, a left-back arm and a right-back arm are A, B, and C, respectively, and the number of entry into each arm was recorded (here, "entry" is defined that both hind paws of a mouse enter an arm, and entry of forepaws only is defined as "not enter"). This is called as a Y-maze.

The number of 3 consecutive different-arm entry was divided by the total number of arm entry minus 1, and multiplied by 100, to determine a percent alternation (for example, when entry is A-B-C-A-B-C-B-A-B-C-A-B-C-A-B-A-B-A, the total number of entry is 17 and the number of 3 consecutive different-arm entry is 11, so that 11÷(17−1)× 100=68.8(%).).

(3) Results

The results are shown in FIG. 5. FIG. 5A shows the sum of entry number of each mouse in each arm and FIG. 5B shows a percent alternation. Whether or not a drug was administered, the number of entry in the Y-maze arm in SAMP8 was more than that in SAMR1, indicating hyperactivity (FIG. 5A). This fact is recognized by the SAM Council. The SAM Council has, therefore, confirmed in its annual meeting that a Y-maze is unsuitable as a test for memory, learning and cognitive ability of the mice. Meanwhile, it has been confirmed by this test that bexarotene or CBt-PMN have no effects on SAMP8 hyperactivity. It has been furthermore confirmed that the effects of CBt-PMN in the step-through test are owing to improvement in cognitive ability.

Example 6

<MRI Imaging of the Brain of a Senescence-Accelerated Mouse (SAMP8) by Administration of an RXR Partial Agonist>

(1) Objective and Mice Used

In mice with declined cognitive ability, atrophy of the hippocampus was anticipated. Thus, MRI imaging of the brain of the mice used in the above study was performed using an MRI imaging device for a small animal (BioSpec, 4.7 Tesla (T)).

(2) Imaging Method

Under isoflurane anesthesia, the head of each mouse was subjected to MRI imaging. Here, the number of mice used were as follows: SAMR1: normal (n=4), CBt-PMN (n=4), SAMP8: vehicle (n=4), CBt-PMN (n=4).

(3) Results

As shown in FIG. 6, the size of the hippocampus of SAMP8 mice was obviously increased by administration of CBt-PMN. Since no differences are observed for the hippocampus of SAMR1 mice between normal and CBt-PMN administration, the effects of CBt-PMN in SAMP8 mice is expected to have correlation with improvement in memory/learning ability observed in the step-through test.

Example 7

<Blood Data and Organ Weight in a Senescence-Accelerated Mouse (SAMP8) after Administrating an RXR Partial Agonist>

(1) Objective and Mice Used

After MRI imaging, the mice used in the above test were subjected to blood collection and then dissected, and blood data and the weight of each organ were recorded. Autopsy was conducted for the mice fed with MF feed containing a drug for 9 weeks. The animals were not fasted the day before the autopsy.

(2) Determining Blood Triglyceride

Plasma was collected from blood taken from the inferior vena cava using a heparin tube, and biochemical data were taken using FUJI DRI-CHEM.

(3) The Number of Samples Used

The number of mice used in each group was as follows:

SAMR1: normal (n=4), bexarotene (n=3), CBt-PMN (n=4)

SAMP8: vehicle (n=4), bexarotene (n=4), CBt-PMN (n=4)

(4) Results

The results are shown in FIG. 7. Here, bex, CBt, n and v in the figure are bexarotene, CBt-PMN, normal and vehicle, respectively. Administration of CBt-PMN induced increase in a brain weight of SAMP8 mice in comparison with the vehicle group, and the weight was comparable to that of a brain weight of SAMR1 mice (FIG. 7A). In the Bexarotene administration group, enlargement of the liver and increase in a blood triglyceride were observed in both SAMR1 and SAMP8 mice. In the CBt-PMN administration group, enlargement of the liver and a blood triglyceride in SAMR1 mice were substantially comparable to the normal group, while for SAMP8 mice, in one of five animals, the values were significantly increased so that tendency to increase was observed in an average, but they seemed to be comparable to normal in comparison with bexarotene (FIG. 7B, C).

Example 8

<Therapeutic Effects of an RXR Partial Agonist in Parkinson's Disease Model Rats>

(1) Animals Used

A 8-week old male SD rat under isoflurane anesthesia was skin-incised on the head and then a connective tissue was dissected and removed. Then, the tissue was fixed on a brain stereotactic fixture, bregma and lambda coordinates were measured, a microinjection cannula was inserted at four points of administration coordinates AP (+1.3, +0.4, −0.4, −1.3 mm) and DV (−5.0 mm) at the depth of 5.0 mm from the brain surface, and 2 µL of a 3.5 mg/mL solution of 6-OHDA (6-hydroxydopamine) in a saline with 0.02% ascorbic acid as a solvent was infused at a rate of 1 µL/min. Similar surgical procedure was conducted for a sham group and saline with ascorbic acid alone was infused. Five minutes after infusion, the glass pipette was kept to be inserted for diffusing the solution. After the surgical procedure, every one week, a body weight was measured, and to the animal, a 1 mg/mL solution of apomorphine in a saline was intraperitoneally administered at 1 mg/kg, the animal was placed at the center of a circular observation box with a diameter of 40 cm and then its rotatory movement was observed for 3 minutes. A rat with Parkinson's disease rotates to the left after apomorphine administration. An individual which rotated seven or more times in one minute after the initiation of the rotation was used as a Parkinson's disease model.

(2) Evaluation Method

The rats were allowed to freely access to MF feed containing a 0.015% w/w RXR partial agonist. After 6 and 12 days, to the animal was intraperitoneally administered a 1 mg/mL solution of apomorphine in saline at 1 mg/kg, and the rotatory movement number for 3 minutes immediately after the administration was recorded.

(3) Results

The following table shows the results at Day 12 after the initiation of administration.

TABLE 2

| Individual identification number | Apomorphine | | OBt-PMN | | NEt-41B | |
|---|---|---|---|---|---|---|
| | Left | Right | Left | Right | Left | Right |
| 1 | 19 | 0 | 61 | 0 | 18 | 0 |
| 2 | 9 | 0 | 17 | 0 | 6 | 0 |
| 3 | 4 | 0 | 63 | 0 | 0 | 75 |
| 4 | 16 | 0 | 40 | 0 | 32 | 0 |
| 5 | 11 | 0 | 9 | 0 | 53 | 0 |
| 6 | | | 15 | 13 | | |

In this model animal, apomorphine triggers characteristic rotational behavior induced by dopamine-like effect (rotational behavior to the un-destructed direction). As shown in Table 2, single dose of apomorphine induced left rotation, while in the group receiving the RXR partial agonist, the rotation number was larger than the apomorphine-administration group, showing therapeutic effects against Parkinson's disease.

Example 9

<Preparation of Multiple Sclerosis Model Mice (EAE Mice) and Drug Efficacy Evaluation Method>

(1) Test Procedure

Seven-week old male C57BL6/J mice were purchased and acclimated for one week. First, a 2 mg/mL aqueous solution of MOG35-55 and a 2 mg/mL aqueous solution of incomplete Freund's adjuvant were mixed in equal amount. Then, the mixture and a 2 mg/mL aqueous solution of M. Tuberculosis H37Ra killed bacteria (Difco) were mixed in equal amount to prepare an emulsion. This emulsion was prepared before use and subcutaneously injected at 200 µL per mouse.

A 100 µg/mL aqueous solution of pertussis toxin (PT) was prepared, and stored as a stock solution (stored at 4° C.). Before administration, this solution was diluted 50 times with PBS to 2 µg/mL, and 200 µL of the resulting solution per mouse was intraperitoneally injected using a double needle for intraperitoneal administration. This procedure was conducted immediately after administration of the above emulsion (Day 0) and the day after next (Day 2).

Animals were allowed to freely access MF feed containing 0.015 w/w % of an evaluated drug, and a daily food intake was determined. Every day from the day of administration (Day 0), clinical scores were recorded, including a body weight, a food consumption, a water consumption and a clinical score (0: normal, 1: tail tonus drop, 2: completely limp tail, 3: gait abnormality, 4: complete weakness of hind paws, 5: complete weakness of hind paws with forepaw paralysis, 6: death).

(2) Results

The results are shown in FIG. 8. FIG. 8A shows the results of a normal group (normal), a drug non-administration group (vehicle) and a bexarotene administration group. FIG. 8B shows the results of a normal group (normal), a drug non-administration group (vehicle) and a CBt-PMN administration group. As shown in FIG. 8, bexarotene which is an RXR full agonist did not ameliorate this pathological model, while CBt-PMN which is an RXR partial agonist exhibited lower clinical scores in comparison with the vehicle group, showing drug efficacy.

The invention claimed is:

1. A method for increasing the activation of Nurr1/RXR, comprising administering an effective amount of an RXR agonist as an active ingredient wherein the RXR agonist is a compound represented by formula (1):

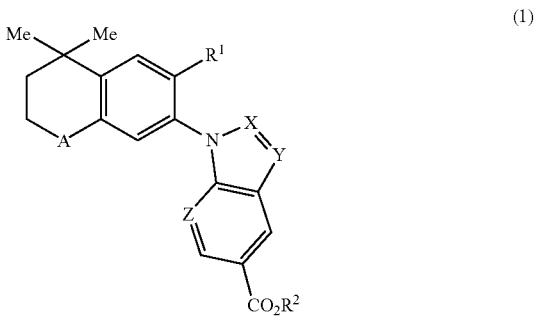

wherein A represents CMe; X represents N; Y represents N; represents CH; $R^1$ represents methyl; and $R^2$ represents H.

2. The method as claimed in claim 1, wherein RXR agonist is effective in inhibiting production nitric oxide.

3. The method as claimed in claim 1, wherein the RXR agonist has Nurr1/RXR activating effect.

4. The method as claimed in claim 1, wherein the RXR agonist is administered in a dosage of about 0.01 to 1000 mg per day.

5. The method of claim 1, wherein the RXR agonist is administered orally or parenterally.

\* \* \* \* \*

UNITED STATES PATENT AND TRADEMARK OFFICE
CERTIFICATE OF CORRECTION

PATENT NO. : 10,285,985 B2  
APPLICATION NO. : 15/562509  
DATED : May 14, 2019  
INVENTOR(S) : Hiroki Kakuta Page 1 of 1

It is certified that error appears in the above-identified patent and that said Letters Patent is hereby corrected as shown below:

Column 16, Line 63: CMe should read -- $CMe_2$ --.

Column 16, Line 64, before the first instance of "represents", -- Z -- should be inserted.

Column 16, Line 66, before "RXR", -- the -- should be inserted.

Column 16, Line 67, before "nitric", -- of -- should be inserted.

Signed and Sealed this  
Twenty-second Day of October, 2019

Andrei Iancu  
*Director of the United States Patent and Trademark Office*